(12) United States Patent
Abecassis

(10) Patent No.: US 11,097,322 B1
(45) Date of Patent: Aug. 24, 2021

(54) AUXIN-ENHANCED PHYTOREMEDIATION PROCESS FOR REMOVAL OF METAL CONTAMINANTS FROM POLLUTED SOIL AND FLY ASH FROM COAL

(71) Applicant: David Abecassis, Huntington Station, NY (US)

(72) Inventor: David Abecassis, Huntington Station, NY (US)

( * ) Notice: Subject to any disclaimer, the term of this patent is extended or adjusted under 35 U.S.C. 154(b) by 183 days.

(21) Appl. No.: 16/406,245

(22) Filed: May 8, 2019

Related U.S. Application Data

(60) Provisional application No. 62/670,736, filed on May 12, 2018.

(51) Int. Cl.
| | | |
|---|---|---|
| *B02C 1/10* | (2006.01) | |
| *B09C 1/10* | (2006.01) | |
| *C12P 19/26* | (2006.01) | |
| *A01G 29/00* | (2006.01) | |
| *C22B 3/18* | (2006.01) | |

(52) U.S. Cl.
CPC .............. *B09C 1/105* (2013.01); *A01G 29/00* (2013.01); *C12P 19/26* (2013.01); *C22B 3/18* (2013.01); *B09C 2101/00* (2013.01)

(58) Field of Classification Search
CPC ....... B09C 1/105; B09C 2101/00; C22B 3/18; A01G 29/00; C12P 19/26
See application file for complete search history.

(56) References Cited

U.S. PATENT DOCUMENTS

| | | | | |
|---|---|---|---|---|
| 2,127,175 A | * | 8/1938 | Imbertson | E02D 19/10 |
| | | | | 47/58.1 R |
| 3,057,116 A | * | 10/1962 | Szochet | A01G 23/02 |
| | | | | 47/58.1 R |
| 5,016,548 A | * | 5/1991 | Ito | A01C 11/02 |
| | | | | 111/114 |
| 5,060,418 A | * | 10/1991 | Pullman | A01G 9/086 |
| | | | | 47/58.1 R |
| 5,157,207 A | * | 10/1992 | Carlson | C12R 1/01 |
| | | | | 800/320.2 |
| 6,189,262 B1 | * | 2/2001 | Gatliff | B09C 1/105 |
| | | | | 47/58.1 R |
| 6,540,436 B2 | * | 4/2003 | Ogi | A01G 29/00 |
| | | | | 239/201 |
| 2003/0196375 A1 | * | 10/2003 | Ferro | A01G 29/00 |
| | | | | 47/58.1 SC |

* cited by examiner

*Primary Examiner* — Edwin J Toledo-Duran
(74) *Attorney, Agent, or Firm* — Thomas A. O'Rourke; Bodner & O'Rourke, LLP

(57) ABSTRACT

The phytoremediation process for removing hazardous metals, such as Be, Cr, Co, Mn, and Ra, from contaminated soil and/or coal fly ash, e.g. in a landfill, includes growing plants in the soil and/or fly ash; incorporating a root growth inducing auxin in the soil and/or fly ash in the vicinity of the growing plants and subsequently cultivating the plants until a predetermined increase in root mass of the plant roots has occurred. The preferred auxin is 3-4-deoxy-glucosamine, which was found to increase plant root mass by 200% to 800%. An organic synthesis using glucosamine as starting material or a bioengineering process starting with commercial micronized shrimp meal and/or crab meal moistened with water can provide the 3-4-deoxy-glucosamine. Economical embodiments of the process use plants that produce marketable products and recovers valuable metals.

21 Claims, No Drawings

AUXIN-ENHANCED PHYTOREMEDIATION PROCESS FOR REMOVAL OF METAL CONTAMINANTS FROM POLLUTED SOIL AND FLY ASH FROM COAL

This utility application claims the benefit of U.S. Provisional Patent Application Ser. No. 62/670,736 filed May 12, 2018 under 35 U.S.C. § 119(e).

FIELD OF THE INVENTION

The present invention relates to improved phytoremediation processes for removing metal contaminates from contaminated soil, especially in landfills, and, more particularly, to economical bioengineering processes for removing, and optionally recovering, hazardous or otherwise harmful metals from contaminated soil and/or fly ash from coal by growing plants in the soil and/or fly ash.

BACKGROUND OF THE INVENTION

Disposal of hazmat material containing hazardous metals, for example disposal of fly ash from coal, is an increasingly pressing problem faced by modern society. These pollutants or hazardous materials may contain various toxic, environmentally damaging, or carcinogenic metals, such as Be, Cr, Co and Mn; radioactive metals, such as Ra; and poisonous substances, such as As.

However recovery of significant quantities of these hazardous or otherwise harmful metals, e.g. from contaminated soil and from fly ash, could be economically beneficial and would help pay for this sort of phytoremediation process. Also harvesting of judiciously chosen plants that are raw materials for marketable products could make such phytoremediation processes even more economical, even profitable.

OBJECTS OF THE INVENTION

It is an object of the invention to provide an improved phytoremediation process for economical removal of metal contaminants from contaminated soil, from coal fly ash, or from hazmat material in landfills by harvesting plants grown in the contaminated soil, the coal fly ash, or in the landfills.

It is a further object of the invention to provide a more effective phytoremediation process for removing carcinogenic, toxic, poisonous, and/or radioactive metal deposits from contaminated soil, fly ash, or landfill by stimulating increases in the mass of roots of plants grown in the contaminated soil, fly ash, or landfill using novel plant growth stimulating auxins.

It is an additional object of the invention to provide a phytoremediation process for recovering harmful metals from the contaminated soil, fly ash, such as fly ash obtained by combustion of coal, by auxin-induced increases in the root mass of roots of the plants grown in the contaminated soil and/or in the fly ash.

It is another object of the invention to provide an economical and even profitable phytoremediation process for removal and recovery of harmful metals, especially of toxic and/or poisonous metals, from contaminated soil, fly ash and/or landfill, by stimulating the growth of roots and absorption of the harmful metals by the roots of plants grown in the contaminated soil, fly ash, or in the landfill.

It is also an object of the invention to provide an economical, and even profitable, phytoremediation process for removal and recovery of toxic and/or poisonous metals, such as Be, B, Mn, and/or Ra, from contaminated soil, fly ash, and/or landfills containing them, by stimulating a substantial increase in the root mass of growing plants by a novel by auxin that stimulates plant growth.

It is a still further object of the invention to provide a means to remediate metals from soil.

Yet another object of the invention is to increase root mass uptake efficiency in plants used in phytoremediation.

A further object of the invention is to remediate coal combustion residue, known as coal flyash.

A still further object of the invention is to couple bioleaching with auxin augmented phytoremediation of metals.

BRIEF SUMMARY OF THE INVENTION

The above objects, and others, which will be made more apparent herein after, will be attained in a phytoremediation process for removing hazardous, toxic, carcinogenic, or otherwise harmful metals from contaminated soil and/or from fly ash, which includes growing plants in the contaminated soil and/or fly ash. The roots of the growing plants will then take up the harmful contaminating metals as they grow.

According to the present invention the novel phytoremediation remediation process for removing hazardous or otherwise harmful metals from the contaminated soil and/or fly ash, such as fly ash from coal, comprises the steps of:

a) growing plants in the contaminated soil and/or fly ash;

b) incorporating a root growth inducing auxin in the contaminated soil and/or fly ash in the vicinity of the plants growing in the contaminated soil and/or fly ash; and c) after the incorporating of step b), cultivating the plants until a predetermined increase in root mass of roots of the growing plants has occurred;

wherein the hazardous metals are toxic, carcinogenic, radioactive or otherwise injurious to living things and/or harmful to the environment For the purposes of the present invention the term "hazardous or otherwise harmful metals" means those metals that are toxic, carcinogenic, radioactive, and/or generally harmful to living things including humans and animals, or to the environment, either directly or indirectly.

In a particularly preferred embodiment of the novel phytoremediation process of the invention the synthetic or natural auxin is a glucosamine or derivative thereof such as 3-4 deoxy-glucosamine. The 3-4-deoxy-glucosamine is a newly discovered plant auxin that stimulates increases in root mass of the roots of the plants that are grown in the contaminated soil and/or fly ash, for example in a landfill in which there are deposits of fly ash powder produced by combustion of coal.

In another embodiment, the invention uses leaching combined with auxin boosted phytoremediation of heavy metals in contaminated soil and media.

Other embodiments of the inventive phytoremediation process can include the use of other root mass increasing auxins that achieve results that are similar to those obtained with 3-4-deoxy-glucosamine.

Tests of the effectiveness of the preferred auxin, 3-4-deoxy-glucosamine, in increasing the root mass of cultivated test plants in comparison to the root mass of the same cultivated test plants, which are grown without the use of any auxin, as a control group, were performed. The results showed that incorporation of 3-4-deoxy-glucosamine in contaminated soil containing hazardous metals in the vicinity of the cultivated test plants stimulated test plant growth by increasing the root mass by 200% to 800% over the root mass of the control group of plants.

Auxins are plant growth hormones. The other auxins that can be used in the inventive phytoremediation process may be naturally occurring or synthetic, but they must result in a greater uptake of the metal contaminants in comparison to uptake of the metal contaminants by a control group of the same plants grown without the presence of auxins in the contaminated soil in the vicinity of the plant roots.

Other well-known auxins (compounds that function as plant hormones) include indole-3-butyric acid (IAA), 1-naphthalene acetic acid (NAA) and indole-3-acetic acid (IAA).

The phytoremediation process according to the invention is especially advantageous when it is applied to clean up landfills in which hazmat deposits of fly ash powder produced by combustion of coal are present. These deposits may contain Be and Cr, listed by OSHA as carcinogenic, Co and Mn which are toxic to humans that inhale them in sufficient quantities, and Ra, which is radioactive. Other contaminating metals such B, Mo, As, Sr, Tl and V may also be present.

In order to cover the costs of the phytoremediation process of the invention, it is especially advantageous when it includes a step of harvesting the plants grown in the contaminated soil and/or fly ash by removing the plants including their roots from the contaminated soil and/or fly ash and then processing the harvested material to recover amounts of individual metals. Radium and Thallium are especially valuable.

The processing to recover the contaminating metals from the harvested crop of plants can take place by chemically processing the roots and/or other parts of the harvested plants, for example by various solvent extraction methods, which would be known to those skilled in the chemical separation and analysis arts. These methods could also include combustion of various parts of the harvested plants followed by chemical processing of the combustion products in an environmentally safe manner.

The use of hemp plants as the plants that are grown in the contaminated soil and/or fly ash would provide valuable products by known manufacturing processes. For example, cannabidiol (CBD) is a valuable legally acceptable product, which costs thousands of dollars a pound and can be obtained by known chemical processes from hemp plants. It is legal in many jurisdictions to grow hemp plants for their industrial products if the hemp plants are strains of *Cannabis satia* that do not contain more than a certain limiting amount of the psychoactive tetrahydrocannabidiol (THC). In addition to cannabidiol, the industrial products of the hemp plant include rope, textiles, clothing, shoes, food, paper, bioplastics, insulation, and biofuel according to the Wikipedia Internet Encyclopedia.

Alternatively Cilantro plants can also be used in the as the plants that are grown in the contaminated soil and/or fly ash in various embodiments of the novel phytoremediation process according to the invention.

Sunflowers can also be used because they are metal over-accumulators

DETAILED DESCRIPTION OF THE INVENTION

A metal over-accumulator plant species is used to remove metals from soil or media by using a plant auxin such as 3.4 deoxy-glucosamine to increase uptake efficiency of metal removal by an roughly an order of magnitude over the control plant of the same species. The plant can also be grown in an open pore bag to absorb metal leachate from bioleaching or leaching water along with its increased root mass efficiency.

In a particularly preferred embodiment of the phytoremediation process according to the invention the step of incorporating the auxin in the contaminated soil and/or fly ash includes spreading the auxin on an upper surface of the soil or fly ash, around the growing plants. Alternatively, the auxin can be included in a fresh nutrient rich soil or culture media that is spread on the contaminated soil and/or fly ash, or on hazmat powder deposits of coal fly ash in a landfill.

Some embodiments of the preferred phytoremediation process according to the invention include control of the cultivation parameters, including the time duration of the cultivation process and the amount of plant auxin incorporated in the contaminated soil, fly ash, or landfill, to maximize the increase in root mass of the harvested crop of plants. The preferred plants are C3 plants. C3 plants are plants in which the initial product of the assimilation of carbon dioxide through photosynthesis is 3-phosphoglycerate, which contains 3 carbon atoms.

An economical and comparatively direct bioengineering process discovered comparatively recently can be used to selectively biosynthesize the preferred auxin, namely 3-4-deoxy-glucosamine, for use in the novel phytoremediation process of the present invention. This bioengineering process and also alternative organic synthesis procedures for obtaining 3-4-deoxy-glucosamine have been described in U.S. patent application Ser. No. 16/244,338 filed Jan. 10, 2019, the disclosures of which are incorporated herein by reference.

This economical bioengineering process includes micronizing commercially obtainable dried shrimp and/or crab meal to form a fine powder, wetting the fine powder with water to form a resulting mixture, and then fermenting the aqueous mixture under aerobic conditions that maximize oxygenation to selectively bloom a Cryptobacteria on the micronized shrimp and/or crab particulate (meal), which then biodegrades and digests the micronized dried shrimp and/or crab meal to exclusively form 3-4-deoxy-glucosamine.

Alternatively a fine powder layer of moistened shrimp and/or crab meal, or particulate thereof, is deposited on a porous substrate in a powder layer that is a few millimeters thick in order to provide maximum aerobic mass exchanges and thus bloom the Cryptobacteria, eventually resulting in digestion and biodegradation of the shrimp and/or crab meal to form the 3-4-deoxy-glucosamine with the properties of an auxin.

Alternative embodiments for obtaining 3-4-deoxy-glucosamine include synthesizing 3-4-deoxy-glucosamine ab initio from small organic molecules, such as glucosamine. Various glycosylation synthesis reactions including direct glycosylation, direct synthesis in the presence of a nucleophilic group, and subsequent reduction and use of glycals as electrophiles in the presence of acid or metals could be employed in a multistep synthetic procedure, if necessary and practical.

One synthesis process utilizes glucosamine as starting material for preparation of 3-4-deoxy-glucosamine. This process may comprise the steps of:
  a) providing a protective group at each hydroxyl bearing carbon atom in glucosamine, except at carbon atoms 3 and 4;
  b) then deoxygenating or reducing the glucosamine with the protective groups attached in the presence of a catalyst so as to remove that oxygen atoms at the carbon atoms 3 and 4; and then c) after the deoxygenating or the reducing of step b) removing the protective groups from the glucosamine to obtain the 3-4-deoxy-glucosamine. Methyl groups are known protective groups; the hydroxyl groups are easily converted to methoxy groups by reagents that provide the methyl groups in a known manner.

Particularly useful phytoremediation processes for removing hazardous metals from contaminated soil and/or fly ash, particularly from hazmat powder piles or stacks of coal fly ash in landfills, comprise:

a) growing plants in the contaminated soil and/or fly ash, wherein the contaminated soil and/or fly ash contain at least one hazardous metal selected from the group consisting of Be, Cr, Co, Mn, Mo, As, Sr, Ra, Tl and V;

b) incorporating 3-4-deoxy-glucosamine as root growth stimulating auxin in the contaminated soil and/or fly ash in the vicinity of the growing plants; and c) after the incorporating of step b), cultivating the plants until a predetermined increase in root mass of roots of the plants and uptake of amounts of the at least one hazardous metal by the plants have occurred; and d) after the cultivating of the plants until a predetermined increase in the root mass and the uptake of the at least one hazardous metal have occurred, harvesting the plants to remove the amounts of the at least one hazardous metal from the soil and/or the fly ash, such as coal fly ash in the landfills.

In a preferred embodiment of the phytoremediation process for removing hazardous metals from contaminated soil and/or fly ash, or from a landfill that contains or covers deposits of coal fly ash, the harvested plants are further chemically and/or physically processed to separate and recover amounts of individual hazardous metals taken up into the plants during their growth. Solvent extraction followed by solvent filtration and evaporation of the solvent are examples of a possible steps of an a recovery process.

It is also advantageous to use plants that provide a valuable harvested crop after the cultivation of the plants to remove the toxic, cancerous, or otherwise harmful metals from the contaminated soil or fly ash. As noted above using hemp plants is especially advantageous, because of the various legal products that can be made from various parts of the plants, such as rope, textiles, clothing, shoes, food, paper, bioplastics, insulation, and biofuel.

EXAMPLES

Example 1: Method of Making
3-4-Deoxy-Glucosamine from Dried Shrimp Meal
and/or Crab Meal The starting material for this method is commercially available dried shrimp meal and/or crab meal. This dried shrimp meal and/or crab meal is micronized and spread out on a porous substrate in a powder layer that is a few millimeters thick to allow maximum aerobic mass exchanges. The powder layer is wet or moistened with water. After from 48 to 72 hours at room temperature a Cryptobacteria blooms on the moistened micronized shrimp meal and/or crab meal and then biodegrades the crustacean meal. The product of this degradation process is the preferred auxin, 3-4-deoxy-glucosamine.

The 3-4-deoxy-glucosamine is leached through a media column and recovered in a pure monomeric form after filtering out any bacteria using a conventional filtration process, such as filtration with diatomaceous earth or with filter paper.

The product of this method was characterized by analytical chemistry procedures, including use of GC/mass spectrometer measurement.

Example 2: Alternative Method of Making
3-4-Deoxy-Glucosamine from Dried Shrimp Meal
and/or Crab Meal The starting material for this alternative method is commercially available dried shrimp meal and/or crab meal. The shrimp meal and/or crab meal is micronized to form a fine powder, which is placed in tap water in a concentration of 5 g/gallon of water. The aqueous mixture is then stirred in a fermenter to form a vortex under maximum oxygenation conditions. After 48 hr. of fermentation, a cryptobacteria blooms on the shrimp and/or crab meal particulate and begins to biodegrade the crustacean meal. The result of this process is a mixture that contains monomers and dimers of 3-4-deoxy-glucosamine in water solution and some of the bacteria and meal particles, which are eventually converted to biomass and the desired monomeric form of 3-4-deoxy-glucosamine.

The monomer can be separated from the aqueous solution phase and characterized, as explained in example 1.

While illustrative examples of one or more embodiments of the present invention are provided hereinabove, those skilled in the art and having the benefit of the present disclosure will appreciate that further embodiments may be implemented with various changes within the scope of the present invention. Other modifications, substitutions, omissions and changes may be made in the choice of plants grown, the root enhancing auxin and its amount, the nature of the contaminated medium, polluted soil or fly ash, in which the plants are grown and the type and amounts of the metal contaminants as well as the process conditions of the phytoremediation process that removes the contaminating metals, without departing from the spirit of the inventive process.

Accordingly, the breadth and scope of the present disclosure should not be limited by any of the above-described exemplary embodiments, but should be defined only in accordance with the following claims and their equivalents.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

Example 3

In one preferred embodiment, hemp plants are grown using 3-4 deoxy glucosamine as an auxin in open-pore bags of granulated coal combustion residue. The cannabinoids can be removed selectively using ethanol extraction, and then the trace metals recuperated from mineralized biomass using acids or chelating agents. The process of growing hemp on the media is repeated until compliant levels of metal residue are reached in the media.

Example 4

In another preferred embodiment hemp is grown using 3-4 deoxy glucosamine in metal and nonmetal element contaminated soil and the soil metal and non-metal element content reduced accordingly.

Example 5

In another preferred embodiment 3-4 deoxy glucosamine is used to amplify the root mass of a plant to remove organic contaminants such as PCB from soil or media or water. The term organics can include synthetic organic contaminants such as aliphatic and polyaromatic hydrocarbons, non biological in origin

What is claimed is new and is set forth in the following appended claims.

I claim:

1. A phytoremediation process for removing hazardous metals from contaminated soil and/or fly ash from coal, wherein said phytoremediation process comprises the steps of:
   a) growing plants in said contaminated soil and/or fly ash containing the hazardous metals;
   b) incorporating a root growth inducing auxin comprising 3-4-deoxy-glucosamine in the contaminated soil and/or fly ash in the vicinity of the plants growing in the contaminated soil and/or fly ash; and
   c) after the incorporating of step b), cultivating the plants until a predetermined increase in root mass of roots of the plants has occurred;
   wherein said hazardous metals are toxic, carcinogenic, radioactive or otherwise harmful to living things and/or to the environment and wherein said 3-4-deoxy-glucosamine is produced from a glucosamine by a separate synthetic chemistry process comprising the steps of:
   i) providing a protective group in said glucosamine at each hydroxyl bearing carbon atom except at carbon atoms 3 and 4; and
   ii) then deoxygenating or reducing the glucosamine with the attached protective groups in the presence of a catalyst in order to remove oxygen atoms at the carbon atoms 3 and 4; and
   iii) after the deoxygenating or the reducing of step b) removing the protective groups from the glucosamine to obtain said 3-4-deoxy-glucosamine.

2. The phytoremediation process according to claim 1, further comprising, after the predetermined increase in the root mass has occurred, harvesting the plants including the roots to recover said hazardous metals that are present in the plants due to uptake of said hazardous metals during cultivation in the presence of the auxin.

3. The phytoremediation process according to claim 2, wherein said plants comprise hemp plants.

4. The phytoremediation process according to claim 3, wherein said hemp plants that are harvested are processed to obtain cannabidiol (CBD).

5. The phytoremediation process according to claim 1, wherein said plants comprise cilantro plants.

6. The phytoremediation process according to claim 1, wherein said hazardous metals are selected from the group consisting of Be, Cr, Co, Mn, Mo, As, Sr, Ra, Tl and V.

7. The phytoremediation process according to claim 1, wherein said fly ash is coal fly ash and said contaminated soil and/or fly ash is located in a landfill.

8. The phytoremediation process according to claim 7, wherein said hazardous metals in said coal fly ash comprise Be, Cr, Co, Mn, and Ra.

9. The phytoremediation process according to claim 1, wherein the incorporating of the auxin in said contaminated soil and/or fly ash includes spreading the auxin or soil containing the auxin on an upper surface of said contaminated soil and/or fly ash around the growing plants.

10. The phytoremediation process according to claim 1, wherein an amount of said 3-4-deoxy-glucosamine and a cultivating time during the cultivating of step c) are chosen, so that said root mass is from 200% to 800% greater than the root mass of said plants grown for the same cultivating time but without incorporating said 3-4-deoxy-glucosamine in said contaminated soil and/or fly ash.

11. The phytoremediation process according to claim 1, further comprising producing said 3-4-deoxy-glucosamine by culturing a fine powder of dried shrimp and/or crab meal that is completely moistened with water under aerobic conditions in order to bloom a cryptobacteria that subsequently degrades and digests the shrimp and/or crab meal to obtain said 3-4-deoxy-glucosamine.

12. The phytoremediation process according to claim 11, wherein the culturing of the fine powder of the shrimp and/or crab meal occurs by spreading the shrimp and/or crab meal on a porous substrate in a powder layer that is a few millimeters thick in order to provide maximum aerobic mass exchanges.

13. The phytoremediation process according to claim 1, further comprising producing said 3-4-deoxy-glucosamine by a fermentation process in which micronized shrimp and/or crab meal is placed in water to form an aqueous mixture and the aqueous mixture is placed in a fermenter and subjected to a vortex under maximum oxygenation in the fermenter for at least 48 hours in order to bloom a cryptobacteria that subsequently degrades and digests the shrimp meal and/or crab meal to obtain said 3-4-deoxy-glucosamine.

14. The phytoremediation process according to claim 13, wherein the micronized shrimp and/or crab meal is added to the water in an amount of 5 grams per gallon.

15. The phytoremediation process according to claim 1, wherein said protective groups are methyl groups.

16. A phytoremediation process for removing hazardous metals from a contaminated landfill, said landfill containing hazmat powder piles or stacks that include fly ash produced by coal combustion, wherein said phytoremediation process comprises the steps of:
   a) growing plants in contaminated soil of the landfill and/or in the hazmat powder plies or stacks that include coal fly ash, wherein said contaminated soil and/or said hazmat powder piles or stacks that include coal fly ash contain at least one hazardous metal selected from the group consisting of Be, Cr, Co, Mn, Mo, As, Sr, Ra, Tl and V;
   b) incorporating 3-4-deoxy-glucosamine in the contaminated soil and/or hazmat powder piles or stacks in the vicinity of the growing plants; and
   c) after the incorporating of step b), cultivating the plants until a predetermined increase in root mass of roots of the plants and uptake of amounts of said at least one hazardous metal by the growing plants have occurred;
   wherein said hazardous metals are toxic, carcinogenic, radioactive or otherwise harmful to living things and/or to the environment and wherein said 3-4-deoxy-glucosamine is produced in a separate synthetic chemistry process comprising the steps of:

i) providing a protective group in said glucosamine at each hydroxyl bearing carbon atom except at carbon atoms 3 and 4; and ii) then deoxygenating or reducing the glucosamine with the attached protective groups in the presence of a catalyst in order to remove oxygen atoms at the carbon atoms 3 and 4; and iii) after the deoxygenating or the reducing of step b) removing the protective groups from the glucosamine to obtain said 3-4-deoxy-glucosamine.

17. The phytoremediation process according to claim 16, further comprising providing said 3-4-deoxy-glucosamine by culturing a fine powder of shrimp and/or crab meal that is completely moistened with water under aerobic conditions, in order to bloom a cryptobacteria that subsequently degrades and digests the shrimp and/or crab meal to obtain said 3-4-deoxy-glucosamine.

18. The phytoremediation process according to claim 17, wherein the fine powder is spread out in a layer that is a few millimeters thick on a porous substrate under maximized aerobic conditions.

19. The phytoremediation process according to claim 17, further comprising producing said 3-4-deoxy-glucosamine by a fermentation process in which micronized shrimp and/or crab meal is placed in water to form an aqueous mixture, the aqueous mixture is placed in a fermenter and the aqueous mixture is subjected to a vortex under maximum oxygenation in the fermenter for at least 48 hours in order to bloom a cryptobacteria that subsequently degrades and digests the shrimp and/or crab meal to obtain said 3-4-deoxy-glucosamine.

20. The phytoremediation process according to claim 19, wherein the shrimp and/or crab meal is added to the water in an amount of 5 grams per gallon.

21. The phytoremediation process according to claim 16, wherein said protective groups are methyl groups.

\* \* \* \* \*